United States Patent
Tsai

(10) Patent No.: US 10,975,392 B2
(45) Date of Patent: Apr. 13, 2021

(54) SITE-DIRECTED CRISPR/RECOMBINASE COMPOSITIONS AND METHODS OF INTEGRATING TRANSGENES

(71) Applicant: ABCAM PLC, Cambridge (GB)

(72) Inventor: Ruby Yanru Tsai, Milpitas, CA (US)

(73) Assignee: ABCAM PLC, Cambridge (GB)

( * ) Notice: Subject to any disclaimer, the term of this patent is extended or adjusted under 35 U.S.C. 154(b) by 0 days.

(21) Appl. No.: 15/533,164

(22) PCT Filed: Dec. 7, 2015

(86) PCT No.: PCT/US2015/064352
§ 371 (c)(1),
(2) Date: Jun. 5, 2017

(87) PCT Pub. No.: WO2016/090385
PCT Pub. Date: Jun. 9, 2016

(65) Prior Publication Data
US 2017/0362611 A1    Dec. 21, 2017

Related U.S. Application Data

(60) Provisional application No. 62/088,440, filed on Dec. 5, 2014.

(51) Int. Cl.
| | |
|---|---|
| *C12N 15/22* | (2006.01) |
| *C12N 15/11* | (2006.01) |
| *C12N 15/90* | (2006.01) |
| *C12N 9/22* | (2006.01) |
| *C12N 9/12* | (2006.01) |

(52) U.S. Cl.
CPC ......... *C12N 15/907* (2013.01); *C12N 9/1241* (2013.01); *C12N 9/22* (2013.01); *C12N 15/11* (2013.01); *C07K 2319/85* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 2014/0295556 A1 | 10/2014 | Joung et al. | |
| 2014/0356867 A1* | 12/2014 | Peter | C12Q 1/6806 435/6.11 |
| 2014/0357530 A1 | 12/2014 | Zhang et al. | |
| 2015/0071898 A1 | 3/2015 | Liu et al. | |

OTHER PUBLICATIONS

Proudfoot et al. Zinc Finger Recombinases with Adaptable DNA Sequence Specificity. Apr. 2011. PLoS ONE. vol. 6, Iss. 4, e19537, 9 pages. (Year: 2011).*
International Search Report of PCT/US2015/064352.
NCBI, PDB: 4CMP_A "SDChain A, Crystal Structure of S. Pyogenes Cas9", Mar. 26, 2014.
NCBI, Reference Sequence: WP_013279315.1, Tn3 resolvase [Enterobacteriaceae], May 18, 2013.

* cited by examiner

*Primary Examiner* — Channing S Mahatan
(74) *Attorney, Agent, or Firm* — Wenderoth, Lind & Ponack, L.L.P.

(57) ABSTRACT

Disclosed herein are targeted chimeric polypeptides, compositions thereof, expression vectors, and methods of use thereof, for the generation of transgenic cells, tissues, plants, and animals. The compositions, vectors, and methods of the present invention are also useful in gene therapy and cell therapy techniques. The chimeric polypeptide includes a CRISPR-Cas domain and a recombinase domain.

9 Claims, 5 Drawing Sheets
Specification includes a Sequence Listing.

```
Tn3 site I (SEQ ID NO: 6)
         ---------CGTTCGAAATATTA|TAAATTATCAGACA---------- res1 (SEQ ID NO: 7)
         -------------AATGCTAATTA|TAAAATAAACA-------------- res2 (SEQ ID NO: 8)
         -------------TTTTCAGACTA|TAAAATGCACA-------------- res3 (SEQ ID NO: 9)
         -------------TATTTGTATTA|TACACTATCTT-------------- res4 (SEQ ID NO: 10)
         -------------CATTTAATTTA|TACTATGGGAA-------------- res5 (SEQ ID NO: 11)
         -------------AAAGGTATTTA|TAAAAGAAGAG-------------- res6 (SEQ ID NO: 12)
         -------------AGCTCAAAGTA|TAGTAGTCAGT--------------
```

FIG. 4

```
C1tn3C1 (SEQ ID NO: 13)
atagccttgtggctaataccaggTCGAAATATTA|TAAATTATCAGcctggtattagccacaaggctat C1res1C1 (SEQ ID NO: 14)
atagccttgtggctaataccaggAATGCTAATTA|TAAAATAAACAcctggtattagccacaaggctat C1res2C1 (SEQ ID NO: 15)
atagccttgtggctaataccaggTTTTCAGACTA|TAAAATGCACAcctggtattagccacaaggctat C1res3C1 (SEQ ID NO: 16)
atagccttgtggctaataccaggTATTTGTATTA|TACACTATCTTcctggtattagccacaaggctat C1res4C1 (SEQ ID NO: 17)
atagccttgtggctaataccaggCATTTAATTTA|TACTATGGGAAcctggtattagccacaaggctat C1res5C1 (SEQ ID NO: 18)
atagccttgtggctaataccaggAAAGGTATTTA|TAAAAGAAGAGcctggtattagccacaaggctat C1res6C1 (SEQ ID NO: 19)
atagccttgtggctaataccaggAGCTCAAAGTA|TAGTAGTCAGTcctggtattagccacaaggctat C1tn3C2  (SEQ ID NO: 20)
atagccttgtggctaataccaggTCGAAATATTA|TAAATTATCAGcccaacaggtcagtttatactg C1res1C2 (SEQ ID NO: 21)
atagccttgtggctaataccaggAATGCTAATTA|TAAAATAAACAcccaacaggtcagtttatactg
```

FIG. 5

SEQUENCE LISTING

<160> NUMBER OF SEQ ID NOS: 21

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
```

```
            785                 790                 795                 800
Val Glu Asn Thr Gln Leu Gln Asn Glu Lys Leu Tyr Leu Tyr Tyr Leu
                        805                 810                 815
Gln Asn Gly Arg Asp Met Tyr Val Asp Gln Glu Leu Asp Ile Asn Arg
                820                 825                 830
Leu Ser Asp Tyr Asp Val Asp His Ile Val Pro Gln Ser Phe Leu Lys
            835                 840                 845
Asp Asp Ser Ile Asp Asn Lys Val Leu Thr Arg Ser Asp Lys Asn Arg
        850                 855                 860
Gly Lys Ser Asp Asn Val Pro Ser Glu Glu Val Val Lys Lys Met Lys
865                 870                 875                 880
Asn Tyr Trp Arg Gln Leu Leu Asn Ala Lys Leu Ile Thr Gln Arg Lys
                        885                 890                 895
Phe Asp Asn Leu Thr Lys Ala Glu Arg Gly Gly Leu Ser Glu Leu Asp
                900                 905                 910
Lys Ala Gly Phe Ile Lys Arg Gln Leu Val Glu Thr Arg Gln Ile Thr
            915                 920                 925
Lys His Val Ala Gln Ile Leu Asp Ser Arg Met Asn Thr Lys Tyr Asp
        930                 935                 940
Glu Asn Asp Lys Leu Ile Arg Glu Val Lys Val Ile Thr Leu Lys Ser
945                 950                 955                 960
Lys Leu Val Ser Asp Phe Arg Lys Asp Phe Gln Phe Tyr Lys Val Arg
                        965                 970                 975
Glu Ile Asn Asn Tyr His His Ala His Asp Ala Tyr Leu Asn Ala Val
                980                 985                 990
Val Gly Thr Ala Leu Ile Lys Lys Tyr Pro Lys Leu Glu Ser Glu Phe
            995                 1000                1005
Val Tyr Gly Asp Tyr Lys Val Tyr Asp Val Arg Lys Met Ile Ala
        1010                1015                1020
Lys Ser Glu Gln Glu Ile Gly Lys Ala Thr Ala Lys Tyr Phe Phe
        1025                1030                1035
Tyr Ser Asn Ile Met Asn Phe Phe Lys Thr Glu Ile Thr Leu Ala
        1040                1045                1050
Asn Gly Glu Ile Arg Lys Arg Pro Leu Ile Glu Thr Asn Gly Glu
        1055                1060                1065
Thr Gly Glu Ile Val Trp Asp Lys Gly Arg Asp Phe Ala Thr Val
        1070                1075                1080
Arg Lys Val Leu Ser Met Pro Gln Val Asn Ile Val Lys Lys Thr
        1085                1090                1095
Glu Val Gln Thr Gly Gly Phe Ser Lys Glu Ser Ile Leu Pro Lys
        1100                1105                1110
Arg Asn Ser Asp Lys Leu Ile Ala Arg Lys Lys Asp Trp Asp Pro
        1115                1120                1125
Lys Lys Tyr Gly Gly Phe Asp Ser Pro Thr Val Ala Tyr Ser Val
        1130                1135                1140
Leu Val Val Ala Lys Val Glu Lys Gly Lys Ser Lys Lys Leu Lys
        1145                1150                1155
Ser Val Lys Glu Leu Leu Gly Ile Thr Ile Met Glu Arg Ser Ser
        1160                1165                1170
Phe Glu Lys Asn Pro Ile Asp Phe Leu Glu Ala Lys Gly Tyr Lys
        1175                1180                1185
Glu Val Lys Lys Asp Leu Ile Ile Lys Leu Pro Lys Tyr Ser Leu
        1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 4104
<212> TYPE: DNA
<213> ORGANISM: Streptococcus pyogenes

<400> SEQUENCE: 2
atggacaaga agtatagcat cgggctggac attggaacga actcggttgg ttgggctgtg      60
attacggacg aatacaaggt gccatccaag aagtttaagg tcctgggaaa caccgaccgt     120
cactcaatca gaagaatctc attggagcc tgctcttcg atagtgggga gaccgccgaa      180
gctactcgac tgaagcgaac ggctcgccgg cgttatacac gacgcaagaa tcgcatctgc     240
tacctccagg agattttcag caacgaaatg gctaaggttg atgactcatt ctttcatcga     300
ctcgaagaaa gtttcttggt cgaggaggat aagaagcacg agcgccatcc gatctttggt     360
aacattgtgg atgaggttgc ctatcacgaa aagtacccaa ctatctatca tcttcgtaag     420
aagctggtcg atagcacgga caaggctgat ttgcgactta tctacctggc actcgcgcac     480
atgattaagt ccgcggcca ttttcttatc gagggtgacc tgaaccccga taattctgac     540
gttgataagc tcttcatcca gttggtccaa acctacaatc agctgtttga ggaaaaccct     600
attaatgcat ctggcgtgga cgccaaggct atcctttcgg cgcgcctgtc taagtcgcgg     660
cgtttggaga accttatcgc acaactcccc ggcgaaaaga gaacggcct cttcggtaat     720 ttgattgcgt tgtcacttgg tctgactcct aacttcaaga gtaattttga cctggcagag     780
gatgcgaagc tccagttgtc taaggatacg tatgatgacg atctcgacaa cttgcttgcc     840
caaatcggtg accagtacgc tgatcttttc ctggccgcta gaatctctc agatgcaatc     900 ctgctcagtg acattttgcg ggtcaacacc gagattacta aggcccccct gtcagctagt     960
atgatcaagc ggtatgatga gcaccatcag gacctcacct tgcttaaggc cctcgtgcgt    1020
cagcaattgc ctgagaagta caaggaaatc ttctttgacc aatccaagaa cggatacgca    1080
gggtatattg atggcggtgc gagccaggag gaattctaca gtttatcaa gccgattttg    1140
```

```
gagaagatgg acggcactga ggaactgctc gtcaagctga atcgcgaaga tttgcttcgt    1200
aagcaacgaa cgttcgacaa cggctccatc ccgcaccaga ttcatctggg cgagctccac    1260
gccatccttc gacgccagga agatttctac ccatttctga aggacaaccg tgagaagatc    1320
gaaaagattc ttacattccg aatccoctac tatgtgggac ctttggcccg tgggaattcc    1380
cgatttgctt ggatgacccg aaagagcgag gaaaccatca ctccgtggaa cttcgaggaa    1440
gtcgtggaca agggtgcatc cgcgcagagc ttcattgagc ggatgaccaa ttttgataag    1500
aaccttccga atgaaaaggt cctgccaaag cattcgctgc tctacgagta tttcaccgtg    1560
tataacgaac tgactaaggt caagtacgtg acggagggaa tgcggaagcc agccttcctc    1620 tcagggaac aaaagaaggc tatcgtcgat ttgcttttta agaccaatcg taaagtgact    1680
gttaagcagc tgaaggagga ttatttcaag aagattgaat gtttcgactc cgtcgagatc    1740
agcggcgtgg aagatcgctt taacgcttcc ctcggtacct accacgacct gctcaagatc    1800
attaaggaca aggatttcct cgataacgag gaaaatgagg acatcttgga agatattgtc    1860
ctcacgttga cacttttga ggaccgcgaa atgatcgagg aacggctcaa gacatatgcc    1920
catttgttcg acgataaggt gatgaagcag ctgaagcggc gtcgatacac cggatggggt    1980
cgccttagcc ggaagctgat aacggcatt cgagataagc aatctggtaa gactatcttg    2040
gatttcctta gtcggacgg cttcgccaac cgcaatttta tgcagcttat tcacgacgat    2100
tccctgacgt tcaaggagga catccagaag gcacaagtct caggacaagg ggattccctg    2160
cacgagcata tcgccaacct ggctggatcc ccggcgatca agaaggggat tcttcagacc    2220
gtcaaggttg tcgacgagct ggtcaaggtg atgggccgtc ataagccaga aaacatcgtg    2280
attgagatgg cccgagaaaa tcagaccact caaaagggtc agaagaacag ccgcgagcgg    2340
atgaagcgga tcgaggaagg cattaaggaa cttggttctc agatcctgaa ggagcaccct    2400
gttgaaaaca cacagctcca aaatgagaag ctgtatctct actatttgca aaatggacgc    2460
gacatgtacg tcgatcagga gctcgacatt aaccggttgt cggactacga tgttgaccat    2520
atcgtcccgc aatccttcct taaggacgat agcattgata caaggtgct gactcgctca    2580 gataagaacc ggggcaagtc cgacaatgtt ccaagcgagg aagtggttaa gaagatgaag    2640
aactactggc gccaattgct taatgccaag ctcatcacac agcgcaagtt tgacaacttg    2700
accaaggccg agcggggagg gctgagtgaa ctcgataagg ctggcttcat caagcgtcaa    2760
ctcgtggaga cgcgacagat cacaaagcac gttgctcaga ttctggactc ccggatgaac    2820
acaaagtacg acgagaatga taagctcatc cgtgaagtta aggtcattac cctcaagtct    2880
aagttggtgt cggatttccg caaggacttc caatttata aggttcggga gatcaacaat    2940
tatcaccatg cacatgatgc gtacctcaac gcagtcgtgg gaactgcgct catcaagaag    3000
tatcccaagt tggagtccga attcgtctac ggggattata aggtttacga cgtccgcaag    3060
atgatcgcca agagtgagca ggaaattggc aaggccacgg ctaagtattt cttttactcc    3120
aacatcatga atttctttaa gacggagatc acactcgcca atggagaaat ccgtaagcga    3180
cctttgattg agaccaacgg cgagactggt gaaatcgttt gggataaggg gcgcgacttc    3240
gctaccgtgc ggaaggttct gagcatgccg caagtcaata tcgtcaagaa accgaggtg    3300 cagacaggcg gtttctctaa ggaatcgatt cttccaaagc gtaactctga caagctgatc    3360
gctcgaaaga aggattggga ccccaagaag tatggagggt tcgattctcc tacagtggca    3420
tactcggttc tcgttgtcgc gaaggttgag aagggaaagt ctaagaagct gaagtcggtc    3480
```

```
aaggaactgc tcgggatcac cattatggag cgctccagct tcgaaaagaa tcccatcgac    3540
tttctcgagg ccaagggcta taaggaagtc aagaaggatc ttatcattaa gctgcctaag    3600
tactctttgt tcgagcttga aaacggtcga aagcgaatgc tcgcatcggc aggagagttg    3660
cagaagggga tgaattggc acttccctca aagtacgtga acttcctgta tctcgcgtcc     3720
cactacgaga agctgaaggg tagccctgag gacaacgaac agaagcaact ttttgttgag    3780
caacacaagc attatctgga tgagatcatt gaacagattt cagagttcag taagcgcgtc    3840
atcctcgccg atgctaatct cgacaaggtg ttgtcggcct acaacaagca ccgtgacaag    3900
ccgatccgag agcaggctga aaatatcatt catctgttca ccctcactaa cttgggagca    3960
ccagcagcgt tcaagtattt tgatacgaca atcgaccgta agcgatacac gtccacaaag    4020
gaggtgcttg atgcgaccct gattcatcaa tccatcactg ggctctatga aacccgtatc    4080
gaccttagtc aactgggggg cgac                                          4104

<210> SEQ ID NO 3
<211> LENGTH: 185
<212> TYPE: PRT
<213> ORGANISM: Escherichia coli

<400> SEQUENCE: 3

Met Arg Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Glu Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Gly Asp Met Gly Gln Met Val Val Thr Ile Leu Ser
            100                 105                 110

Ala Val Ala Gln Ala Glu Arg Arg Arg Ile Leu Glu Arg Thr Asn Glu
        115                 120                 125

Gly Arg Gln Glu Ala Lys Leu Lys Gly Ile Lys Phe Gly Arg Arg Arg
    130                 135                 140

Thr Val Asp Arg Asn Val Val Leu Thr Leu His Gln Lys Gly Thr Gly
145                 150                 155                 160

Ala Thr Glu Ile Ala His Gln Leu Ser Ile Ala Arg Ser Thr Val Tyr
                165                 170                 175

Lys Ile Leu Glu Asp Glu Arg Ala Ser
            180                 185

<210> SEQ ID NO 4
<211> LENGTH: 148
<212> TYPE: PRT
<213> ORGANISM: Artificial Sequence
<220> FEATURE:
<223> OTHER INFORMATION: Tn Resolvase catalytic domain

<400> SEQUENCE: 4

Met Arg Leu Phe Gly Tyr Ala Arg Val Ser Thr Ser Gln Gln Ser Leu
1               5                   10                  15
```

```
Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Glu Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Gly Asp Met Gly Gln Met Val Val Thr Ile Leu Ser
            100                 105                 110

Ala Val Ala Gln Ala Glu Arg Arg Ile Leu Glu Arg Thr Asn Glu
        115                 120                 125

Gly Arg Gln Glu Ala Lys Leu Lys Gly Ile Lys Phe Gly Arg Arg Arg
    130                 135                 140

Thr Val Asp Arg
145

<210> SEQ ID NO 5
<211> LENGTH: 148
<212> TYPE: PRT
<213> ORGANISM: Artificial Sequence
<220> FEATURE:
<223> OTHER INFORMATION: Mutant of Tn Resolvase catalysic domain

<400> SEQUENCE: 5

Met Ala Leu Phe Gly Tyr Ala Arg Val Ser Thr Ser Gln Gln Ser Leu
1               5                   10                  15

Asp Leu Gln Val Arg Ala Leu Lys Asp Ala Gly Val Lys Ala Asn Arg
            20                  25                  30

Ile Phe Thr Asp Lys Ala Ser Gly Ser Ser Thr Asp Arg Glu Gly Leu
        35                  40                  45

Asp Leu Leu Arg Met Lys Val Lys Glu Gly Asp Val Ile Leu Val Lys
    50                  55                  60

Lys Leu Asp Arg Leu Gly Arg Asp Thr Ala Asp Met Ile Gln Leu Ile
65                  70                  75                  80

Lys Glu Phe Asp Ala Gln Gly Val Ala Val Arg Phe Ile Asp Asp Gly
                85                  90                  95

Ile Ser Thr Asp Ser Tyr Ile Gly Leu Met Phe Val Thr Ile Leu Ser
            100                 105                 110

Ala Val Ala Gln Ala Glu Arg Arg Ile Leu Glu Arg Thr Asn Glu
        115                 120                 125

Gly Arg Gln Glu Ala Lys Leu Lys Gly Ile Lys Phe Gly Arg Arg Arg
    130                 135                 140

Thr Val Asp Arg
145

<210> SEQ ID NO 6
<211> LENGTH: 28
<212> TYPE: DNA
<213> ORGANISM: Streptococcus pyogenes

<400> SEQUENCE: 6
cgttcgaaat attataaatt atcagaca                                           28

<210> SEQ ID NO 7
```

```
<211> LENGTH: 22
<212> TYPE: DNA
<213> ORGANISM: Artificial Sequence
<220> FEATURE:
<223> OTHER INFORMATION: Tn3 resolvase variant res1

<400> SEQUENCE: 7
aatgctaatt ataaaataaa ca                                                  22

<210> SEQ ID NO 8
<211> LENGTH: 22
<212> TYPE: DNA
<213> ORGANISM: Artificial Sequence
<220> FEATURE:
<223> OTHER INFORMATION: Tn3 resolvase variant res2

<400> SEQUENCE: 8
ttttcagact ataaaatgca ca                                                  22

<210> SEQ ID NO 9
<211> LENGTH: 22
<212> TYPE: DNA
<213> ORGANISM: Artificial Sequence
<220> FEATURE:
<223> OTHER INFORMATION: Tn3 resolvase variant res3

<400> SEQUENCE: 9
tatttgtatt atacactatc tt                                                  22

<210> SEQ ID NO 10
<211> LENGTH: 22
<212> TYPE: DNA
<213> ORGANISM: Artificial Sequence
<220> FEATURE:
<223> OTHER INFORMATION: Tn3 resolvase variant res4

<400> SEQUENCE: 10
catttaattt atactatggg aa                                                  22

<210> SEQ ID NO 11
<211> LENGTH: 22
<212> TYPE: DNA
<213> ORGANISM: Artificial Sequence
<220> FEATURE:
<223> OTHER INFORMATION: Tn3 resolvase variant res5

<400> SEQUENCE: 11
aaaggtattt ataaagaag ag                                                   22

<210> SEQ ID NO 12
<211> LENGTH: 22
<212> TYPE: DNA
<213> ORGANISM: Artificial Sequence
<220> FEATURE:
<223> OTHER INFORMATION: Tn3 resolvase variant res6

<400> SEQUENCE: 12
agctcaaagt atagtagtca gt                                                  22

<210> SEQ ID NO 13
<211> LENGTH: 68
<212> TYPE: DNA
<213> ORGANISM: Artificial Sequence
<220> FEATURE:
<223> OTHER INFORMATION: C1tn3C1 mutant

<400> SEQUENCE: 13
```
atagccttgt ggctaatacc aggtcgaaat attataaatt atcagcctgg tattagccac    60
aaggctat                                                              68

<210> SEQ ID NO 14
<211> LENGTH: 68
<212> TYPE: DNA
<213> ORGANISM: Artificial Sequence
<220> FEATURE:
<223> OTHER INFORMATION: C1res1C1 mutant

<400> SEQUENCE: 14
atagccttgt ggctaatacc aggaatgcta attataaaat aaacacctgg tattagccac    60
aaggctat                                                              68

<210> SEQ ID NO 15
<211> LENGTH: 68
<212> TYPE: DNA
<213> ORGANISM: Artificial Sequence
<220> FEATURE:
<223> OTHER INFORMATION: C1res2C1 mutant

<400> SEQUENCE: 15
atagccttgt ggctaatacc aggttttcag actataaaat gcacacctgg tattagccac    60
aaggctat                                                              68

<210> SEQ ID NO 16
<211> LENGTH: 68
<212> TYPE: DNA
<213> ORGANISM: Artificial Sequence
<220> FEATURE:
<223> OTHER INFORMATION: C1res3C1 mutant

<400> SEQUENCE: 16
atagccttgt ggctaatacc aggtatttgt attatacact atcttcctgg tattagccac    60
aaggctat                                                              68

<210> SEQ ID NO 17
<211> LENGTH: 68
<212> TYPE: DNA
<213> ORGANISM: Artificial Sequence
<220> FEATURE:
<223> OTHER INFORMATION: C1res4C1 mutant

<400> SEQUENCE: 17
atagccttgt ggctaatacc aggcatttaa tttatactat gggaacctgg tattagccac    60
aaggctat                                                              68

<210> SEQ ID NO 18
<211> LENGTH: 68
<212> TYPE: DNA
<213> ORGANISM: Artificial Sequence
<220> FEATURE:
<223> OTHER INFORMATION: C1res5C1 mutant

<400> SEQUENCE: 18
atagccttgt ggctaatacc aggaaaggta tttataaaag aagagcctgg tattagccac    60
aaggctat                                                              68

<210> SEQ ID NO 19
<211> LENGTH: 68
<212> TYPE: DNA

```
<213> ORGANISM: Artificial Sequence
<220> FEATURE:
<223> OTHER INFORMATION: C1res6C1 mutant

<400> SEQUENCE: 19
atagccttgt ggctaatacc aggagctcaa agtatagtag tcagtcctgg tattagccac    60
aaggctat                                                              68

<210> SEQ ID NO 20
<211> LENGTH: 68
<212> TYPE: DNA
<213> ORGANISM: Artificial Sequence
<220> FEATURE:
<223> OTHER INFORMATION: C1tn3C2 mutant

<400> SEQUENCE: 20
atagccttgt ggctaatacc aggtcgaaat attataaatt atcagcccca acaggtcagt    60
ttatactg                                                              68

<210> SEQ ID NO 21
<211> LENGTH: 68
<212> TYPE: DNA
<213> ORGANISM: Artificial Sequence
<220> FEATURE:
<223> OTHER INFORMATION: C1res1C2 mutant

<400> SEQUENCE: 21
atagccttgt ggctaatacc aggaatgcta attataaaat aaacacccca acaggtcagt    60
ttatactg                                                              68
```

SITE-DIRECTED CRISPR/RECOMBINASE COMPOSITIONS AND METHODS OF INTEGRATING TRANSGENES

CROSS-REFERENCE TO RELATED APPLICATIONS

This application is the national phase of PCT/US2015/064352, filed Dec. 7, 2015, which claims priority to U.S. provisional patent application no. 62/088,440, filed Dec. 5, 2014, the disclosure of which is incorporated herein by reference.

FIELD OF THE INVENTION

The present invention generally relates to compositions and methods used for integrating transgenes into the genome of a cell.

BACKGROUND OF THE INVENTION

RNA-guided Cas9 nucleases derived from clustered regularly interspaced short palindromic repeats (CRISPR)-Cas systems have provided a versatile tool for editing the genome of diverse organisms. However, current technologies based on CRISPR-Cas system have limited ability of inserting large DNA fragments and are unable to perform homology-based editing such as targeted transgene insertion in non-dividing cells (e.g., neurons) or in cells with DNA homologous recombination deficiency. Therefore, there remains a need for new genome engineering technologies that are affordable, easy to set up and capable of editing genome in non-dividing cells or cells with DNA homologous recombination deficiency.

BRIEF SUMMARY OF THE INVENTION

Disclosed herein are targeted chimeric polypeptides, including compositions thereof, expression vectors, and methods of use thereof, for the generation of transgenic cells, tissues, plants, and animals. The compositions, vectors, and methods of the present invention are also useful in gene therapy and cell therapy techniques.

In one aspect, the present disclosure relates to a chimeric polypeptide. The polypeptide includes: 1) a CRISPR-Cas domain and 2) a recombinase domain. In various embodiments, the CRISPR-Cas domain is capable of binding to a guide RNA, which is capable of hybridizing to a target DNA sequence, and the recombinase domain comprises a site-specific recombinase, a mutant thereof or a fragment thereof In some embodiments, the CRISPR-Cas domain comprises a Type-II Cas9 protein (SEQ ID NO: 1) or a fragment thereof. In certain embodiments, the CRISPR-Cas domain does not have endonuclease activity. In certain embodiments, the CRISPR-Cas domain is a catalytically dead Cas9 (dCas9). In certain embodiments, the CRISPR-Cas domain comprises an amino acid sequence of SEQ ID NO: 1.

In some embodiments, the recombinase domain comprises a site-specific recombinase. In some embodiments, the site-specific recombinase is a tyrosine recombinase. Examples of the tyrosine recombinase include, but are not limited to, Cre, Flp and the lambda integrase. In some embodiments, the site-specific recombinase is a serine recombinase. Examples of the serine recombinases include gamma-delta resolvase, Tn3 resolvase (SEQ ID NO: 2), Sin resolvase, Gin invertase, Hin invertase, Tn5044 resolvase, IS607 transposase and integrase. In some embodiments, the site-recombinase is an integrase selected from the group consisting of Bxb1, wBeta, BL3, phiR4, A118, TG1, MR11, phi370, SPBc, TP901-1, phiRV, FC1, K38, phiBT1 and phiC31 (SEQ ID NO: 3).

In certain embodiments, the recombinase domain comprises a mutant version or a fragment of a site-specific recombinase as disclosed above. In certain embodiments, the mutant has altered target specificity. In some embodiments, the mutant has reduced target specificity. In certain embodiments, the recombinase domain comprises an activated mutant of a recombinase, including but without limitation activated mutant of Tn3 and activated mutant of phiC31. In certain embodiments, the recombinase domain is a catalytic domain of an activated mutant of a recombinase. In certain embodiments, the recombinase domain comprises a catalytic domain of activated mutant of Tn3. In certain embodiments, the recombinase domain has an amino acid sequence selected from the group consisting of SEQ ID NO: 5 and the variants thereof as listed in Table 1.

In certain embodiments, the polypeptide further comprises a linker that links the CRISPR-Cas domain and the recombinase domain. In certain embodiments, the linker has an amino acid sequence of The-Ser.

In anther aspect, the present application discloses a composition comprising the polypeptide as disclosed above, and the guide RNA. In certain embodiment, the composition further comprises a donor DNA including a first nucleotide sequence recognized by a site-specific recombinase and a transgene.

In yet another aspect, the present application discloses a composition comprising one or more vectors comprising (i) a first nucleotide sequence encoding the polypeptide as disclosed above; and (ii) a second nucleotide sequence encoding the guide RNA, wherein the first and second nucleotide are located on same or different vectors. In certain embodiments, the composition further comprises a donor DNA comprising a third nucleotide sequence recognized by the polypeptide as disclosed above and a transgene. In certain embodiments, the composition further comprises a fourth nucleotide sequence encoding the site-specific recombinase.

Another aspect of the present application relates to a method of integrating a transgene into the genome of a cell. In certain embodiments, the method comprises introducing into the cell the composition as disclosed above. In certain embodiments, the cell is a eukaryotic cell, e.g., a mammalian or human cell. In certain embodiments, the cell is a one-cell embryo.

These and other features, aspects, and advantages of the present invention will become better understood with regard to the following description, appended claims and accompanying drawings.

BRIEF DESCRIPTION OF THE FIGURES

FIG. 4 illustrates Tn3 res site I and the six 22 bp TATA-containing sequences similar to Tn3 res site I, which are aligned with the central TATA of site I. Bases identical to site I within the central 12 bp of the TATA-containing sequences are underlined.

FIG. 5 illustrates sequences of site I and C-sites.

DETAILED DESCRIPTION OF THE INVENTION

Figure 1:
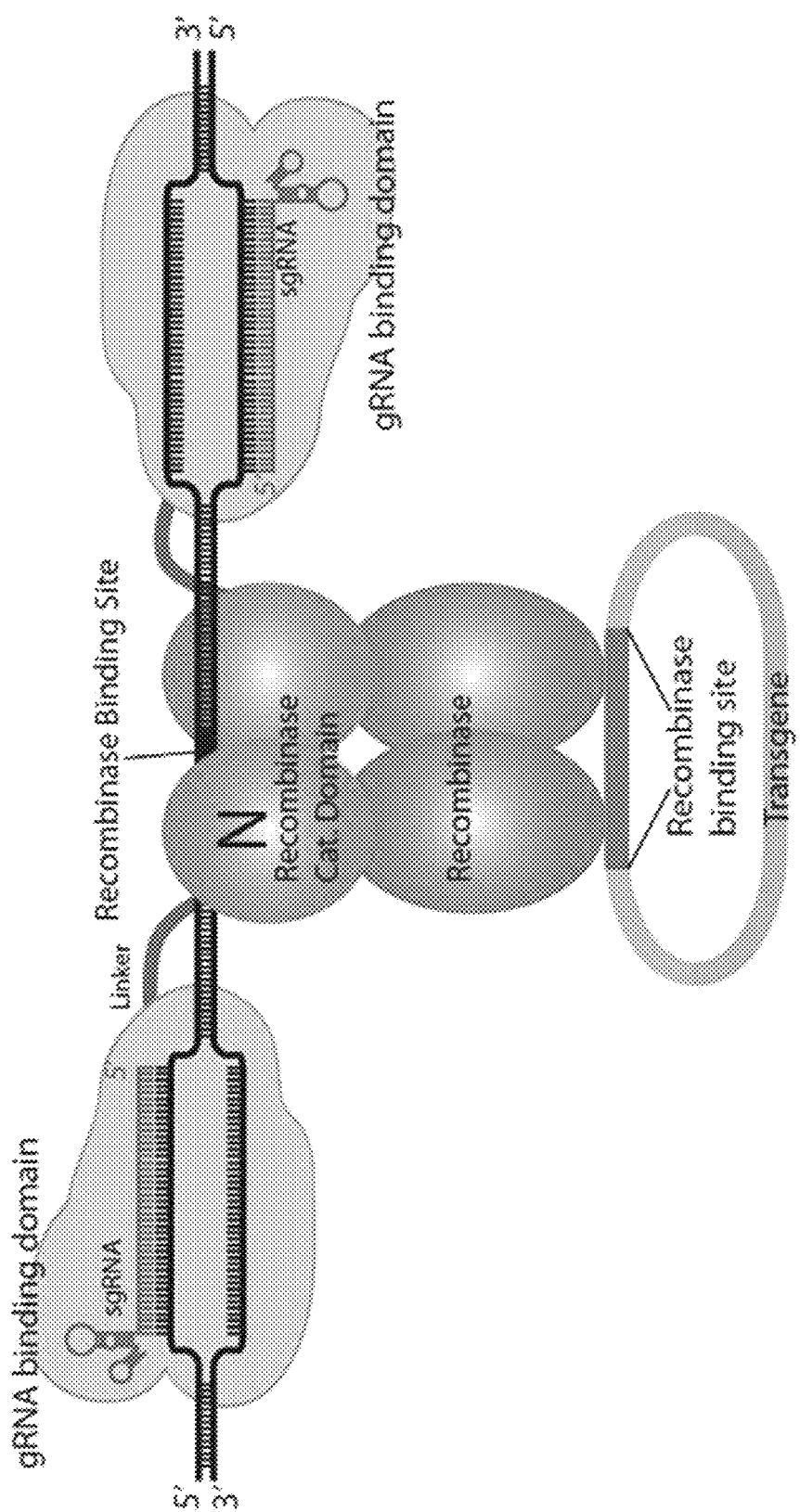
FIG. 1 is a schematic illustration of the complex of gRNA-directed Cas-recombinase chimeric polypeptide (CasR comlex) formed at the target sequence to mediate the recombination between the donor DNA and the target DNA. Typically, the target DNA include a sequence (the target site) similar to a recombinase recognition site. The complex comprises two chimeric polypeptides (CasR), each of which includes a CRISPR-Cas domain (gRNA binding domain) and a recombinase domain. The CRISPR-Cas domain is capable of binding to a guide RNA. The Cas domain and the recombinase domain are linked by a peptide linker. Upon binding to guide RNA(s) that hybridizes to sequences flanking the target site, two CasRs are recruited to the target site, respectively, wherein the recombinase domains form a dimer at the target site. A tetramer of recombinase or recombinase domain is then formed at the target site and activated by binding to its cognate sites, and mediates the recombination between the donor DNA and the target DNA.
Figure 2A:
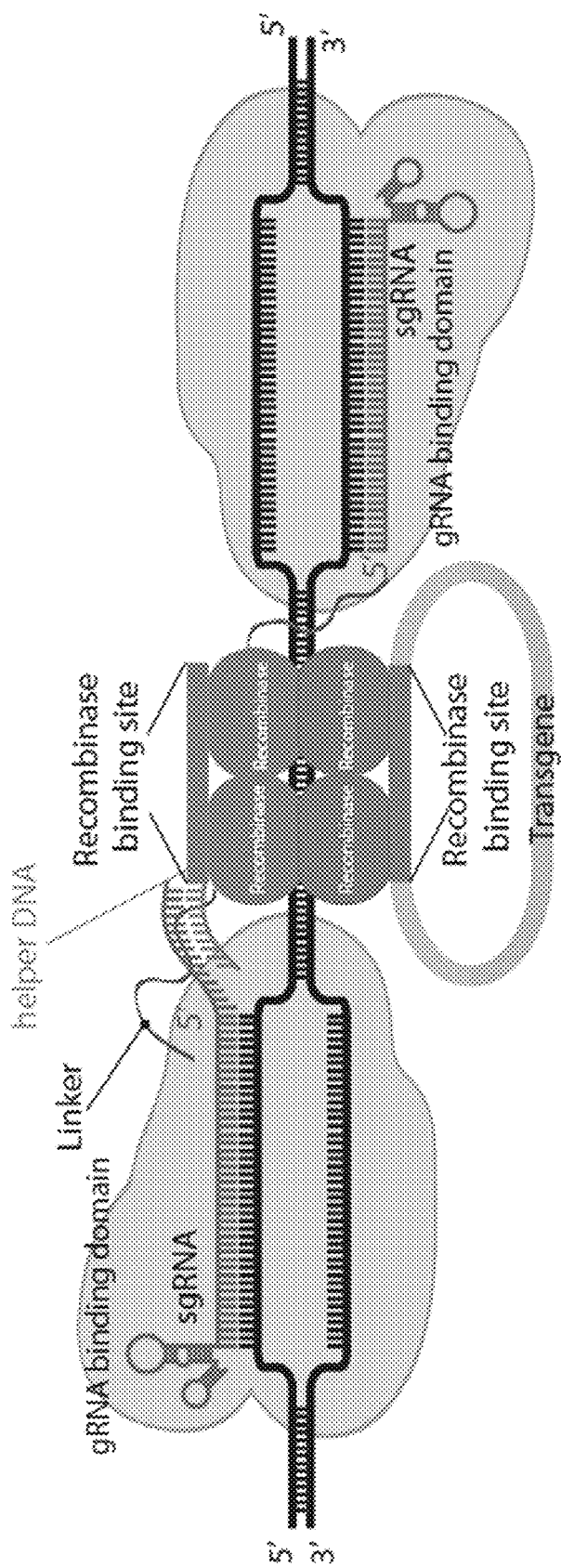
FIG. 2A is another embodiment of the complex of site-directed recombinase formed at the target sequence to mediate the recombination between the donor DNA and the target DNA. The complex comprises a first CRISPR-Cas system guide RNA that hybridizes with a first sequence in the target DNA, a second CRISPR-Cas system guide RNA that hybridize with a second sequence in the target DNA and at least two site-directed modifying polypeptides comprising a guide-RNA-binding domain that is capable of binding to the first or second CRISPR-Cas system guide RNA, and a recombinase domain. The gRNA binding domain and recombinase domain are linked by a peptide linker. Upon binding to the guide RNA through the guide-RNA-binding domain, the site-directed modifying polypeptides are recruited to the target sequence. A tetramer of recombinase or recombinase domain is formed at the target sequence and activated by binding to its cognate sites, and mediates the recombination between the donor DNA and the target DNA. The cognate sites are either located on a helper DNA or on a donor vector.
Figure 2B:
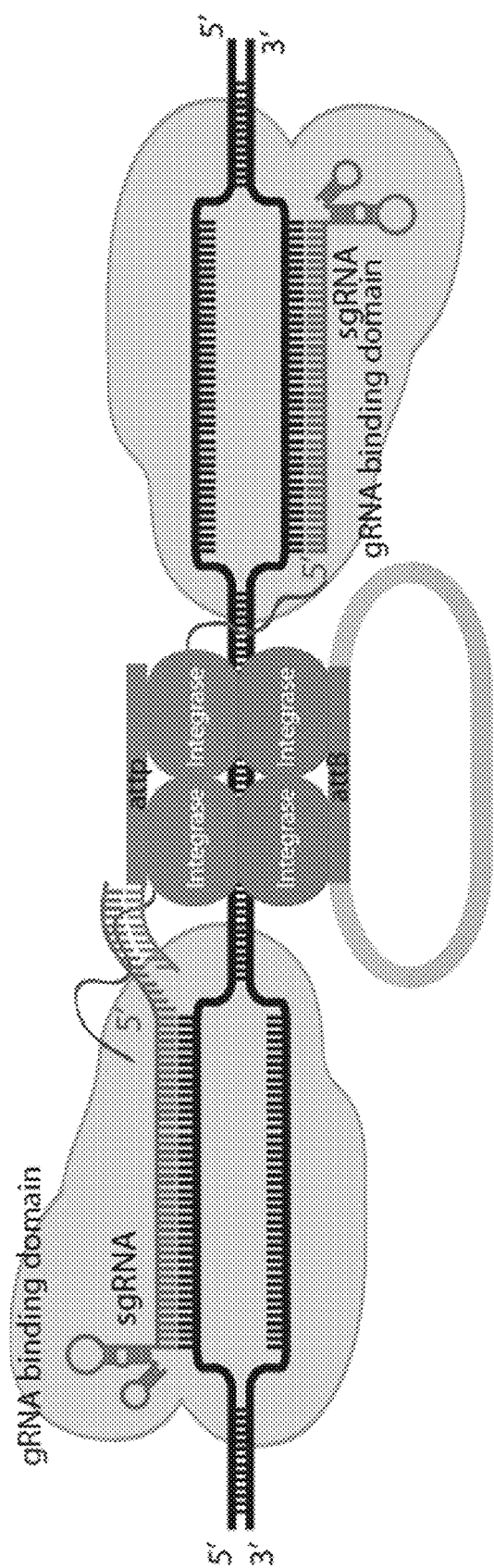
FIG. 2B illustrates another embodiment of the complex of site-directed recombinase formed at the target sequence to mediate the recombination between the donor DNA and the target DNA. Integrase is used as an example to illustrate how site-directed CRISPR/recombinase works for transgene insertion. Upon binding to the guide RNA through the guide-RNA-binding domain, the site-directed modifying polypeptides are recruited to the target sequence. A tetramer of integrase or a domain thereof, or a variant with altered target specificity is formed at the target sequence and activated by binding to its cognate sites, attP and attB, and mediates the recombination between the donor DNA and the target DNA. The attP site is located on a helper DNA or attB site is on a donor vector.

In the Summary of the Invention above and in the Detailed Description of the Invention, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Where a range of value is provided, it is understood that each intervening value, to the tenth of the unit of the lower limit unless the context clearly dictate otherwise, between the upper and lower limit of that range and any other stated or intervening value in that stated range, is encompassed within the disclosure, subject to any specifically excluded limit in the stated range. Where the stated range includes one or both of the limits, ranges excluding either or both of those included limits are also included in the disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, the embodiments described herein can be practiced without their specific details. In other instances, methods, procedures and components have not been described in detail so as not to obscure the related relevant function being described. Also, the description is not to be considered as limiting the scope of the implementations described herein. It will be understood that descriptions and characterizations of the embodiments set forth in this disclosure are not to be considered as mutually exclusive, unless otherwise noted.

The following definitions are used in the disclosure:

The terms "nucleic acid molecule" and "polynucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers.

As used herein, the term "vector" refers to a nucleic acid molecule capable of transporting between different genetic environments another nucleic acid to which it has been operatively linked. Preferred vectors are those capable of autonomous replication and expression of structural gene products present in the DNA segments to which they are operatively linked. Vectors, therefore, preferably contain the replicons and selectable markers described earlier. Vectors include, but are not necessarily limited to, expression vectors.

As used herein, the term "expression vector" refers to a plasmid, virus, phagemid, or other vehicle known in the art that has been manipulated by insertion or incorporation of heterologous DNA, such as nucleic acid encoding the fusion proteins herein or expression cassettes provided herein. Such expression vectors typically contain a promoter sequence for efficient transcription of the inserted nucleic acid in a cell. The expression vector typically contains an origin of replication, a promoter, as well as specific genes that permit phenotypic selection of transformed cells.

In one aspect, the present disclosure provides a CRISPR-Cas recombinase (CasR), which can be used to recombine DNA in bacterial and mammalian cell. The CasR includes a CRISPR-Cas domain and a recombinase domain. The CRISPR-Cas domain mediates the recognition of the CasR to a specific target sequence via a guide RNA, and the recombinase domain carries out the recombination.

As used herein, the term "recombinase" or "site-specific recombinase" refers to a family of highly specialized enzymes that promote DNA rearrangement between specific target sites (Greindley et al., 2006; Esposito, D., and Scocca, J. J., Nucleic Acids Research 25, 3605-3614 (1997); Nunes-Duby, S. E., et al, Nucleic Acids Research 26, 391-406 (1998); Stark, W. M., et al, Trends in Genetics 8, 432-439 (1992)). Virtually all site-specific recombinases can be categorized within one of two structurally and mechanistically distinct groups: the tyrosine (e.g., Cre, Flp, and the lambda integrase) or serine (e.g, phiC31 integrase, gamma-delta resolvase, Tn3 resolvase and Gin invertase) recombinases. Both recombinase families recognize target sites composed of two inversely repeated binding elements that flank a spacer sequence where DNA breakage and religation occur. The recombination process requires concomitant binding of two recombinase monomers to each target site: two DNA-bound dimers (a tetramer) then join to form a synaptic complex, leading to crossover and strand exchange. "Hyperactive" forms of Tn3 resolvase containing activating mutations in Tn3 resolvase can catalyze strand exchange at a core site of 28 bp without accessory sites, presumably through reconfiguration of the tertiary/quaternary structure of the tetramer.

"Site-directed recombinase activity" or "site-directed recombination" as used herein refers to the sequence specific recombination of a first nucleic acid sequence with a second nucleic acid sequence, typically mediated by a site-specific recombinase. In general, site-specific recombination occurs at particular defined sequences recognized by the recombinase. In contrast to random integration, site-directed recombinase occurs at a particular sequence (e.g., a recombinase attachment site) at a higher efficiency.

In certain embodiments, the site-specific recombinase is Tn3 resolvase. In certain embodiments, the site-specific recombinase is Gin Invertase. In certain embodiments, the site-specific recombinase is an integrase selected from Bxb1, wBeta, BL3 phiR4, A118, TG1, MR11, phi370, SPBc, TP901-1, phiRV, FC1, K38, phiBT1 and phiC31.

In some embodiments, the recombinase domain comprises a variant (mutant) of a site-specific recombinase or a fragment thereof, wherein the variant has altered target specificity. Methods have been established to change the target specificity of a recombinase. For example, Buchholz and Stewart utilized random mutagenesis by error-prone PCR, DNA shuffling, and a lacZ-based blue/white recombination screen to generate Flp variants with enhanced thermostability (Buchholz et al., 1998). In another example, accessory-factor independent variants of the lambda-Integrase have been identified by selection in the presence of defective integration host factor activity (Miller et al., 1980) and reversion analysis (Wu et al., 1997). In yet another example, Voziyanov et al. (2002) developed a dual-reporter screen that enabled direct readout of the effects of individual mutations on Flp specificity and identified a number of Flp variants with altered target specificity. In another example, Buchholze and Stewart developed a technique termed Substrate-Linked Protein Evolution (SLiPE) to physically link individual recombinase variants to their DNA substrate (Buchholz and Stewart, 2001). In some embodiments, the variant of the site-specific recombinase has a reduced target specificity.

More recently, mutants of several serine recombinases, e.g., Tn3 have been identified that do not require accessory factors for recombination (Proudfoot et al., 2001, Zinc Finger Recombinases with Adaptable DNA Sequence Specificity. PloS ONE 6 (4): e19537). It was shown that the native DNA binding domains (DBDs) of serine recombinases can be replaced with custom-designed ZFPs to generate chimeric zinc-finger recombinases (ZFRs). ZFRs are composed of an activated catalytic domain derived from the resolvase/invertase family of serine recombinases and a zinc-finger DNA-binding domain that can be custom-designed to recognize almost any DNA sequence. ZFRs catalyze recombination between specific ZFR target sites that consist of two-inverted zinc-finger binding sites (ZFBS) flanking a central 20-bp core sequence recognized by the recombinase catalytic domain. In contrast to zinc-finger nucleases (ZFNs) and TAL effector nucleases (TALENs), ZFRs function autonomously and can excise and integrate transgenes in human and mouse cells without activating the cellular DNA damage response pathway. In principle, ZFRs capable of recognizing an extended number of sequences could be generated, however, the lack of zinc-finger domains capable of recognizing all possible DNA triplets limits the potential modular targeting capacity of these enzymes.

In a peptide or protein, suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity (see, e.g. Watson et al. Molecular Biology of the Gene, 4th Edition, 1987, Benjamin/Cummings, p. 224). In particular, such a conservative variant has a modified amino acid sequence, such that the change(s) do not substantially alter the protein's (the conservative variant's) structure and/or activity, e.g., antibody activity, enzymatic activity, or receptor activity. These include conservatively modified variations of an amino acid sequence, i.e., amino acid substitutions, additions or deletions of those residues that are not critical for protein activity, or substitution of amino acids with residues having similar properties (e.g., acidic, basic, positively or negatively charged, polar or non-polar, etc.) such that the substitutions of even critical amino acids does not substantially alter structure and/or activity. Conservative substitution tables providing functionally similar amino acids are well known in the art. For example, one exemplary guideline to select conservative substitutions includes (original residue followed by exemplary substitution): Ala/Gly or Ser; Arg/Lys; Asn/Gln or His; Asp/Glu; Cys/Ser; Gln/Asn; Gly/Asp; Gly/Ala or Pro; His/Asn or Gln; Ile/Leu or Val; Leu/Ile or Val; Lys/Arg or Gln or Glu; Met/Leu or Tyr or He; Phe/Met or Leu or Tyr;

Ser/Thr; Thr/Ser; Trp/Tyr; Tyr/Trp or Phe; Val/Ile or Leu. An alternative exemplary guideline uses the following six groups, each containing amino acids that are conservative substitutions for one another: (1) alanine (A or Ala), serine (S or Ser), threonine (T or Thr); (2) aspartic acid (D or Asp), glutamic acid (E or Glu); (3) asparagine (N or Asn), glutamine (Q or Gln); (4) arginine (R or Arg), lysine (K or Lys); (5) isoleucine (I or He), leucine (L or Leu), methionine (M or Met), valine (V or Val); and (6) phenylalanine (F or Phe), tyrosine (Y or Tyr), tryptophan (W or Trp); (see also, e.g., Creighton (1984) Proteins, W. H. Freeman and Company; Schulz and Schimer (1979) Principles of Protein Structure, Springer-Verlag). One of skill in the art will appreciate that the above-identified substitutions are not the only possible conservative substitutions. For example, for some purposes, one may regard all charged amino acids as conservative substitutions for each other whether they are positive or negative. In addition, individual substitutions, deletions or additions that alter, add or delete a single amino acid or a small percentage of amino acids in an encoded sequence can also be considered "conservatively modified variations" when the three-dimensional structure and the function of the protein to be delivered are conserved by such a variation.

In general, "CRISPR-Cas system" or "CRISPR system" refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or other sequences and transcripts from a CRISPR locus. In some embodiments, one or more elements of a CRISPR system is derived from a type I, type II, or type III CRISPR system. In some embodiments, one or more elements of a CRISPR system are derived from a particular organism comprising an endogenous CRISPR system, such as *Streptococcus pyogenes*. In general, a CRISPR system is characterized by elements that promote the formation of a CRISPR complex at the site of a target sequence (also referred to as a protospacer in the context of an endogenous CRISPR system).

In general, a "CRISPR-Cas guide RNA" or "guide RNA" refers to an RNA that directs sequence-specific binding of a CRISPR complex to the target sequence. Typically, a guide RNA comprises (i) a guide sequence that has sufficient complementarity with a target polynucleotide sequence to hybridize with the target sequence and (ii) a trans-activating cr (tracr) mate sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

In the context of formation of a CRISPR complex, a "target sequence" or "a sequence of a target DNA" refers to a sequence to which a guide sequence is designed to have complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides or DNA/RNA hybrid polynucleotides. In some embodiments, a target sequence is located in the nucleus or cytoplasm of a cell. In some embodiments, the target sequence may be within an organelle of a eukaryotic cell, for example, mitochondrion or chloroplast.

A guide sequence may be selected to target any target sequence. In some embodiments, the target sequence is a sequence within a genome of a cell. Exemplary target sequences include those that are unique in the target genome. For example, for the *S. pyogenes* Cas9, a unique target sequence in a genome may include a Cas9 target site of the form MMMMMMMMMNNNNNNNNNNNNXGG where NNNNNNNNNNNNXGG (N is A, G, T, or C; and X can be any nucleotide) has a single occurrence in the genome. For the *S. thermophilus* CRISPR1Cas9, a unique target sequence in a genome may include a Cas9 target site of the form MMMMMMMMMNNNNNNNNNNNNXXAGAAW where NNNNNNNNNNNNXXAGAAW (SEQ ID NO: 2) (N is A, G, T, or C; X can be any nucleotide; and W is A or T) has a single occurrence in the genome. In each of these sequences "M" may be A, G, T, or C, and need not be considered in identifying a sequence as unique.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106 (1): 23-24; and P A Carr and G M Church, 2009, *Nature Biotechnology* 27(12): 1151-62).

As used herein, a tracr mate sequence includes any sequence that has sufficient complementarity with a tracr sequence to promote one or more of: (1) excision of a guide sequence flanked by tracr mate sequences in a cell containing the corresponding tracr sequence; and (2) formation of a CRISPR complex at a target sequence, wherein the CRISPR complex comprises the tracr mate sequence hybridized to the tracr sequence. In general, degree of complementarity is with reference to the optimal alignment of the tracr mate sequence and tracr sequence, along the length of the shorter of the two sequences. Optimal alignment may be determined by any suitable alignment algorithm, and may further account for secondary structures, such as self-complementarity within either the tracr sequence or tracr mate sequence. In some embodiments, the degree of complementarity between the tracr sequence and tracr mate sequence along the length of the shorter of the two when optimally aligned is about or more than about 25%, 30%, 40%, 50%, 60%, 70%, 80%, 90%, 95%, 97.5%, 99%, or higher.

In some embodiments, the guide RNA comprises a guide sequence fused to a tracr sequence, i.e., the tracr sequence and tracr mate sequence are contained within a single transcript, such that hybridization between the two produces a transcript having a secondary structure, such as a hairpin. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. Preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG. In an embodiment of the present application, the guide RNA has at least two or more hairpins. In preferred embodiments, the guide RNA has two, three, four or five hairpins. In a further embodiment of the invention, the guide RNA has at most five hairpins. In some embodiments, the guide RNA further includes a transcription termination sequence, preferably a polyT sequence, for example six T nucleotides. In some embodiments, the tracr sequence is a separate transcript from a transcript comprising the tracr mate sequence.

In some embodiments, the CRISPR-Cas domain comprises a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1,Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csxl, Csx15, Csf1, Csf2, Csf3, Csf4, homologs thereof, or modified versions thereof. These enzymes are known; for example, the amino acid sequence of *S. pyogenes* Cas9 protein (SEQ ID NO: 1) may be found in the SwissProt database under accession number Q99ZW2. In some embodiments, the unmodified Cas protein has DNA cleavage activity. In some embodiments, the Cas protein directs cleavage of one or both strands at the location of a target sequence, such as within the target sequence and/or within the complement of the target sequence. In some embodiments, the Cas protein directs cleavage of one or both strands within about 1, 2, 3, 4, 5, 6, 7, 8, 9, 10, 15, 20, 25, 50, 100, 200, 500, or more base pairs from the first or last nucleotide of a target sequence. In some embodiments, the Cas protein is mutated such that the mutated Cas protein lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). Other examples of mutations that render Cas9 a nickase include, without limitation, H840A, N854A, and N863A. In some embodiments, the fragment of the Cas protein lacks DNA cleavage activity, e.g., the fragment does not contain the catalytic domain of the Cas protein (e.g., RuvC I, RuvC II, and RuvC III domain of Cas9). In some embodiments, two or more catalytic domains of Cas9 (RuvC I, RuvC II, and RuvC III) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas protein is considered to substantially lack all DNA cleavage activity when the DNA cleavage activity of the mutated enzyme is less than about 25%, 10%, 5%, 1%, 0.1%, 0.01%, or lower with respect to its non-mutated form. Other mutations may be useful; where the Cas9 or other Cas protein is from a species other than *S. pyogenes*, mutations in corresponding amino acids may be made to achieve similar effects.

In some embodiments, the site of recombinase activity is determined by the CRISPR-Cas system guide RNA. Upon binding to the guide RNA, the site-directed modifying polypeptide is directed to the target sequence and exerts a recombinase activity in the presence of a recombination site of the recombinase such as integrase attachment sites, attP and attB. For example, a Cas9 guide RNA can direct a polypeptide comprising a Cas9 and a phiC31 to form a complex at a target sequence. In the presence of its cognate attP and attB sites, phiC31 integrase is activated to mediate a site-specific recombination between a donor DNA and the target sequence, resulting in an integration of a DNA sequence into the target sequence.

In some embodiments, the donor DNA comprises a transgene to be inserted at the target sequence and a wild-type recombination attachment site of the integrase.

A "recombination site" as used herein means a recombination site recognized and used by a recombinase. For example, lambda is a temperate bacteriophage that infects E. coli. The phage has one attachment site for recombination (attP) and the *E. coli* bacterial genome has an attachment site for recombination (attB). Both of these sites are wild-type recombination sites for lambda integrase. In the context of the present invention, wild-type recombination sites occur in the homologous phage/bacteria system. Accordingly, wild-type recombination sites can be derived from the homologous system and associated with heterologous sequences, for example, the attB site can be placed in other systems to act as a substrate for the integrase.

In some embodiments, the integrase in the site-directed modifying polypeptide is bacteria phage phiC31. The wild-type attB and attP recognition sites of phage phiC31 are generally about 34 to 40 nucleotides in length (Groth et al. *Proc Natl Acad Sci USA* 97:5995-6000 (2000)). These sites are typically arranged as follows: AttB comprises a first DNA sequence attB5', a core region, and a second DNA sequence attB3' in the relative order from 5' to 3' attB5'-core region-attB3'. AttP comprises a first DNA sequence attP5', a core region, and a second DNA sequence attP3', in the relative order from 5' to 3' attP5' —core region-attP3'. The core region of attP and attB of phiC31 has the sequence 5'-TTG-3'.

In some embodiments, the composition further comprises a helper DNA comprising a second nucleotide sequence recognized by the site-specific recombinase. The helper DNA is contemplated to facilitate the formation of a complex comprising the guide RNA, one or more site-directed modifying polypeptide at the target DNA sequence, wherein the complex is functional in mediating a recombination between the donor DNA and the target DNA, resulting in an insertion of a DNA sequence in the donor DNA into the target DNA. In some embodiments, the helper DNA hybridizes with a sequence in the guide RNA. In this scenario, in the presence of the helper DNA, at least two recombinase domains that bind to the second nucleotide sequence at the donor DNA interact with at least two recombinase domain that bind to the first nucleotide sequence at the help DNA, thus forming a tetramer that functions to facilitate a crossover and strand exchange between the donor DNA and the target DNA.

In some embodiments, the composition further comprises a recombinase or a fragment thereof. Upon binding to the guide RNA through the guide-RNA-binding domain, the site-directed modifying polypeptides are recruited to the target sequence. A tetramer of recombinase or recombinase domain is formed at the target sequence and activated by binding to its cognate sites, and mediates the recombination between the donor DNA and the target DNA.

In some embodiments, the composition further comprises a second CRISPR-Cas system guide RNA that is capable of hybridizing with a second sequence in the target DNA. The second sequence in the target DNA is separated from the first sequence in the target DNA by about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50 nucleotide.

In another aspect, the present application discloses a composition comprising one or more vectors comprising (i) a first nucleotide sequence encoding a polypeptide as disclosed above; and (ii) a second nucleotide sequence encoding a guide RNA.

As used herein, the term "vector" refers to a polynucleotide molecule that comprises a gene or a nucleic acid sequence of particular interest. Typically, the construct also includes appropriate regulatory sequences. For example, the polynucleotide molecule can include regulatory sequences located in the 5'-flanking region of the nucleotide sequence encoding the guide RNA and/or the nucleotide sequence encoding a site-directed modifying polypeptide, operably linked to the coding sequences in a manner capable of expressing the desired transcript/gene in a host cell.

The vector comprising the nucleotide sequence encoding the guide RNA and/or the nucleotide sequence encoding a site-directed modifying polypeptide can be prepared using methods well known in the art. For example, the polynucleotide molecule can be prepared as part of a larger plasmid. Such preparation allows the cloning and isolation of the correct constructs in an efficient manner as is known in the art. The various methods employed in the preparation of the plasmids and transformation of host organisms are known in the art (see, e.g., Molecular Cloning A Laboratory Manual, 2nd Ed., ed. By Sambrook, Fritsch and Maniatis, Cold Spring Harbor Laboratory Press, 1989).

In some embodiments, the one or more vectors further comprise a nucleotide sequence encoding a recombinase. Upon binding to the guide RNA through the guide-RNA-binding domain, the site-directed modifying polypeptides are recruited to the target sequence. A tetramer of recombinase or recombinase domain or recombinase variant activated by binding to its cognate sites, or a tetramer of activated recombinase is formed at the target sequence and activated by binding to its cognate binding sites, and mediates the recombination between the donor DNA and the target DNA.

In yet another aspect, the present application discloses a method of integrating a DNA sequence into the genome of a cell comprising introducing into the cell a composition comprising one or more vectors comprising: (i) a first nucleotide sequence encoding a first CRISPR-Cas system guide RNA, wherein the first guide RNA is capable of hybridizing with a first sequence in a target DNA; and (ii) a second nucleotide sequence encoding a site-directed modifying polypeptide, wherein the site-directed modifying polypeptide comprising: (a) a guide-RNA-binding portion that is capable of binding to the guide RNA; and (b) a recombiase domain; (iii) a donor DNA comprising: (a) a third nucleotide sequence recognized by the site-specific recombinase; and (b) the transgene.

In some embodiments, one or more vectors comprising the nucleotide sequence encoding the guide RNA and/or the nucleotide sequence encoding a site-directed modifying polypeptide are introduced into a host cell such that expression of the elements of the composition direct formation of a complex at the target sites. For example, the complex comprises a first CRISPR-Cas system guide RNA that hybridizes with a first sequence in the target DNA, a second CRISPR-Cas system guide RNA that hybridize with a second sequence in the target DNA and at least two site-directed modifying polypeptides comprising a guide-RNA-binding domain and a recombinase domain. Upon binding to the guide RNA through the guide-RNA-binding domain, the site-directed modifying polypeptides are recruited to the target sequence. A tetramer of recombinase domain is formed at the target sequence and activated by binding to its cognate sites, and mediates the recombination between the donor DNA and the target DNA.

Conventional viral and non-viral based gene transfer methods can be used to introduce the vectors in mammalian cells, target tissues or one-cell embryos. Such methods can be used to administer nucleic acids encoding components of the composition to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome, protein complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6 (10):1149-1154 (1988); Vigne, Restorative Neurology and Neuroscience 8:35-36 (1995); Kremer & Perricaudet, British Medical Bulletin 51 (1):31-44 (1995); Haddada et al., in Current Topics in Microbiology and Immunology Doerfler and Bihm (eds) (1995); and Yu et al., Gene Therapy 1:13-26 (1994).

Methods of non-viral delivery of nucleic acids include lipofection, nucleofection, electroporation, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Microinjection is used to deliver DNA, RNA or peptides into a nucleus and cytoplasm of a one-cell embryo. It is well known to one of skill in the art (see Manipulating the mouse embryo; A laboratory manual, fourth edition, 2014).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (in vivo). Conventional viral based systems could include retroviral, lentiviral, adenoviral, adeno-associated and herpes simplex viral vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700). In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

Packaging cells are typically used to form virus particles that are capable of infecting a host cell. Such cells include 293 cells, which package adenovirus, and ψ2 cells or PA317 cells, which package retrovirus. Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences. The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, U.S.20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject such as a primary cell or a stem cell. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A 172, A20, A253, A431, A-549, ALC, B16, B35, BCP-1 cells, BEAS-2B, bEnd.3, BHK-21, BR 293. BxPC3. C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK 11, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassus, Va.)). In some embodiments, a cell transfected with one or more vectors described herein is used to establish a new cell line comprising one or more vector-derived sequences. In some embodiments, a cell transiently transfected with the components of the composition as described herein (such as by transient transfection of one or more vectors, or transfection with RNA, or transfection with protein), and modified through the activity of the complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

EXAMPLE 1

This example illustrates an active CasR mutant including variant of chimeric Cas9 protein and a catalytic domain of active mutant of Tn3 resolvase (CasTn3). CasTn3's capability of mediating recombination is tested in a recombination assay using a substrate plasmid containing a sequence, Tn3 res site I, recognized and bound by CasTn3. The potential target sequence (C-site) comprises 22 bp of Tn3 res site I flanked by 17 bp motifs recognized by dCas9 domain via suitable gRNA. The substrate plasmid is then constructed in which two identical C-sites are separated by a galK marker gene. If CasTn3-mediated recombination in *E. coli* cells deletes galK, the colonies on MacConkey-galactose indicator plates are pale, whereas galK+ colonies are red.

Expression plasmids for 'progenitor' CasTn3 are generated as follows. A resolvase expression plasmid with a p15a origin of replication (pEK76) is derived from pACYC184 (Chang A C, Cohen S N (1978) Construction and characterization of amplifiable multicopy DNA cloning vehicles derived from the P15A cryptic miniplasmid. J Bacteriol 134: 1141-1156.), by insertion of an SspI-EcoRV resolvase-encoding fragment from pAT5 (Arnold P H, Blake D G, Grindley N D F, Boocock M R, Stark W M (1999) Mutants of Tn3 resolvase which do not require accessory binding sites for recombination activity. EMBO J 18: 1407-1414.) into the pACYC184 AvaI site. CasTn3 expression plasmids (pCasTn3) are then created by insertion of ORF-containing fragments of dCas9 between unique NdeI and Asp718 sites in pEK76.

The 'progenitor' CasTn3 used here consists of the Tn3 resolvase catalytic domain (residues 1-148) containing the seven mutations R2A E56K G101S D102Y M103I Q105L V107F, followed by the 2-amino acid linker TS, then the dCas9. The codons for the TS linker introduce a unique SpeI restriction site.

Figure 3:
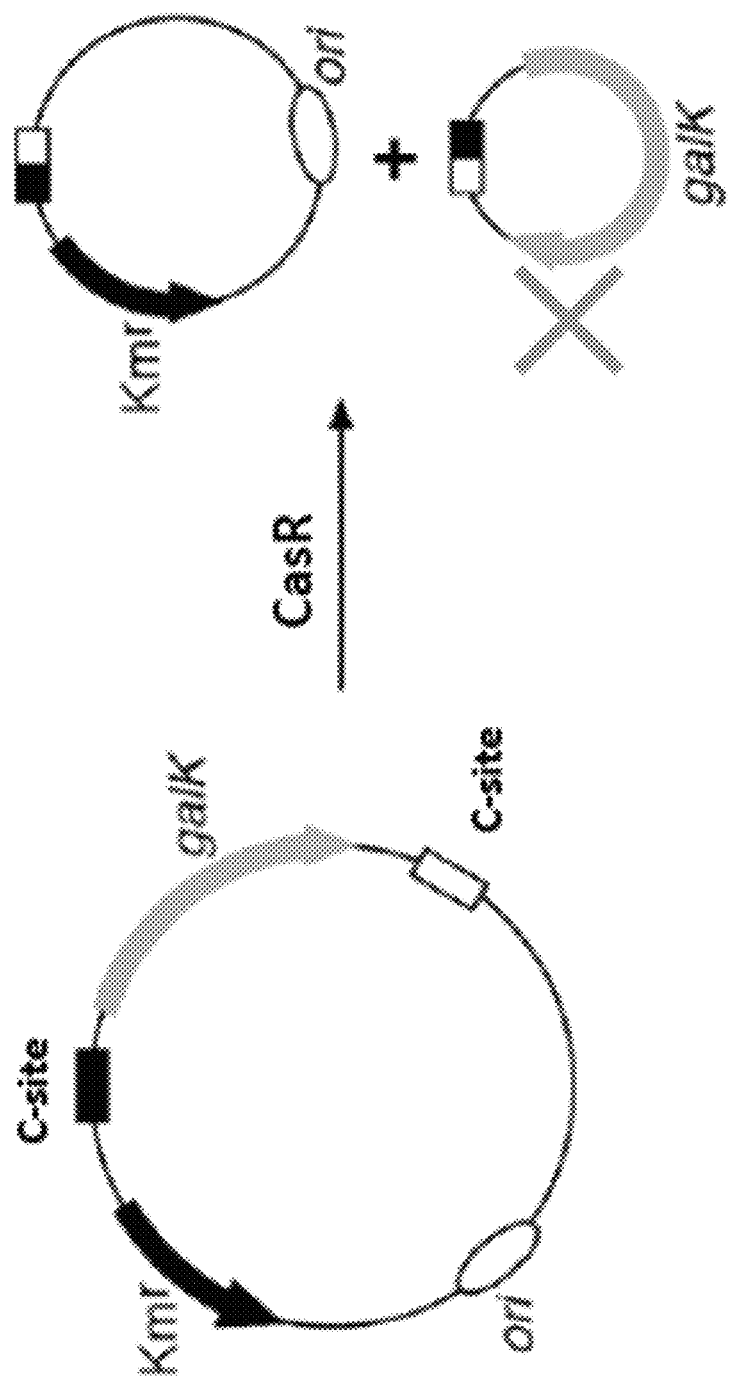
FIG. 3 illustrates *E. coli* colony color assays of recombination used to test the capability of CasR to mediate recombination of C-sites. Strains containing a substrate plasmid are co-transformed with a CasR expression plasmid and a gRNA expression plasmid. Transformants are selected on MacConkey-galactose indicator plates (MacConkey agar base (Difco) supplemented with 1% galactose, kanamycin (to select for the substrate plasmid or its resolution product), and ampicillin and/or chloramphenicol (to select for pCasR expression plasmids). Pale coloured (galK$^-$) colonies indicate recombination (resolution) proficiency, whereas red (galK+) colonies indicate lack of resolution.

The C-site, which is designed to be recognized by CasTn3, consists of 22bp of Tn3 res site I flanked by 20 bp motifs recognized by dCas9. The sequences of the C-sites used here (C1tn3C1) are shown in FIG. 5. Recombination substrate plasmid, with two C-sites flanking a galK marker gene, is shown in FIG. 3.

*E. coli* colony color assays of recombination are then used to test the capability of CasTn3 to mediate recombination of C-sites. The *E. coli* colony color assay of recombination has been described in Akopian A, He J, Boocock M R, Stark W M (2003) Chimeric recombinases with designed DNA sequence recognition. Proc Natl Acad Sci USA 100: 8688-8691. Briefly, strains containing a substrate plasmid are co-transformed with a CasTn3 expression plasmid and a gRNA expression plasmid. Transformants are selected on MacConkey-galactose indicator plates (MacConkey agar base (Difco) supplemented with 1% galactose, kanamycin (to select for the substrate plasmid or its resolution product), and ampicillin and/or chloramphenicol (to select for pCasTn3 expression plasmids). Pale coloured (galK−) colonies indicate recombination (resolution) proficiency, whereas red (galK+) colonies indicate lack of resolution.

To analyze the DNA products of recombination, strains containing a substrate plasmid are co-transformed with a CasTn3 expression plasmid and a gRNA expression plasmid. Transformants are grown with appropriate antibiotic selection on L-agar plates. Following incubation at 37° C., cells are washed from the plates with L-broth, and plasmid DNA is purified from the cells using a Qiagen miniprep kit. The DNA is visualized by ethidium staining after 1.2% agarose gel electrophoresis. To quantify the extent of recombination (leading to deletion of the galK gene) more accurately, the recovered plasmid DNA is used to transform the strain DS941, test plasmid-containing transformants are selected on MacConkey agar plates with kanamycin, and the percentage of pale (galK−) colonies (from a total of >100) is determined.

The results show that C1Tn3C1 is resolved by CasTn3.

EXAMPLE 2

This example demonstrates that CasTn3 can be used to target asymmetric C-sites. The substrate plasmid used here is similar to that in Example 1 except that it contains a C-site consisting of 22bp of Tn3 res site I flanked by two different 17 bp motifs recognized by dCas9. The sequence of the C-site used here (C1tn3C2) is shown in FIG. 4.

To test CasTn3's capability of recombination targeting asymmetric C-site, strains containing the substrate plasmid are co-transformed with a CasTn3 expression plasmid and two gRNA expression plasmids that express gRNA recognizing C1 and C2 respectively. Transformants are selected on MacConkey-galactose indicator plates (MacConkey agar base (Difco) supplemented with 1% galactose, kanamycin (to select for the substrate plasmid or its resolution product), and ampicillin and/or chloramphenicol (to select for pCasTn3 expression plasmids and gRNA expression plasmids, respectively). Pale coloured (galK−) colonies indicate recombination (resolution) proficiency, whereas red (galK+) colonies indicate lack of resolution.

The DNA products of recombination are analyzed as in Example 1.

The result shows that CasTn3 can mediate recombination at asymmetric C-sites.

EXAMPLE 3

This example illustrates identification of CasTn3 variants that would promote recombination at potential target sequence similar but not identical to Tn3 res site I.

In general, a series of potential target sequences that are similar to Tn3 res site I, and which might be optimal for resolvase activity are used (shown in FIG. 4). These potential target sequences are over 12 bp centered on the TATA motif and include at least 8 out of 12 base pairs identical to one orientation. "C1resC1" site are made, each comprising 22 bp of a potential Tn3 res site flanked by 17 bp motifs recognized by dCas9 domain via corresponding gRNA.

To find CasTn3 variants that can promote recombination at the potential C1resC1 sites, the entire catalytic domain of Tn3 is subject to random mutagenesis using two error-prone PCR protocols, and made libraries of plasmids expressing mutant CasTn3s are made (see Burke M E, Arnold P H, He J, Wenwieser S V C T, Rowland S J, et al. (2004) Activating mutations of Tn3 resolvase marking interfaces important in recombination catalysis and its regulation. Mol Microbiol 51: 937-948.). To screen for recombination-proficient CasTn3 mutants, DS941 cells containing a recombination substrate plasmid are transformed with a library of mutant expression plasmids and gRNA expression plasmids. Aliquots of the transformants are selected on MacConkey plates (aiming for ~1000 colonies per plate; 30-60 plates). Pale-colored colonies are picked and are streaked on MacConkey plates to confirm the colony color. Plasmid DNA purified from positive isolates is used to transform the same DS941-substrate plasmid strain. If the transformant colonies on MacConkey plates are all pale-colored, the CasTn3 is deemed to be a recombination-proficient mutant, so the expression plasmid is isolated and the CasTn3 reading frame is sequenced.

Screens of the libraries using C1resC1 substrate plasmids yields several active mutants as shown in Table 1 below. Recovery of DNA from the cells show that one mutant with the single conservative change I77L has significant recombination activity on C1resC1 substrates.

The mutagenesis-screening procedure can be repeated, using newly identified CasTn3 mutant as the template for mutagenesis, and other C1resC1 test substrate. Several active mutants are isolated which are shown to promote efficient recombination of the C1resC1 sites. The mutations thus broaden rather than switch specificity.

in the MacConkey agar colony assay, using substrates with two identical CresC sites as indicated. W, 'white' (pale-colored) colonies; R, red colonies.

EXAMPLE 4

This example illustrates CasR-mediated recombination between non-identical sites.

For transgene integration at any chosen genomic locus, only one of the recombination sites (the genomic one) must be targeted by 'designer' CasRs. The other site (on the transgenic DNA) could be acted on by any recombinase with a compatible catalytic domain, and could be optimized for integration efficiency and specificity. To model this scenario, substrates with non-identical pairs of sites are generated. The C1tn3C1 site contains at its center 22 bp of the natural target sequence for CasTn3 catalytic domains (Tn3 res site I), and a substrate with two of these sites is therefore recombined efficiently. To analyze recombination between C1tn3C1 and other non-identical sites, a set of six C1tn3C1xC1res1C1 are made, in which res1 represents variants of the 22 bp center of the natural target sequence for CasTn3. These plasmids are recombined efficiently.

In order to show that the partner site need not be a C-site, substrates which contained a C1res1C1 site paired with Tn3 res site I is made. Recombination of C1resC1xsite I substrates is efficient when both an activated Tn3 resolvase variant (NM resolvase; Olorunniji F J, He J, Wenwieser S V C T, Boocock M R, Stark W M (2008) Synapsis and catalysis by activated Tn3 resolvase mutants. Nucleic Acids Res 36: 7181-7191.) and a CasTn3-1 are co-expressed, whereas NM resolvase alone or CasTn3-1 alone do not promote recombination.

Finally, a substrate is designed to model transgene integration as outlined above, where one "genomic" recombination site is targeted by the combined action of two gRNA, and the other "transgene" site is recognized by an activated recombinase. For the "genomic" site we chose to use C1res1C2. For the "transgene" site Tn3 res site I is used, as

TABLE 1

Active mutants that promote recombination at potential target sequence.

| Mutant | C-site | | | | | | |
|---|---|---|---|---|---|---|---|
| CasTn3 | C1tn3C1 | C1res1C1 | C1res2C1 | C1res3C1 | C1res4C1 | C1res5C1 | C1res6C1 |
| I77L | W | W | R | R | R | R | R |
| F83L F107L | W | W | W | R | W | W | R |
| I3T D95E | W | W | R | R | W | R | R |
| G70S F107L | W | W | W | R | W | W | R |
| E57G A89V | W | W | W | R | W | W | R |
| K37R D44N | W | W | W | R | W | W | R |
| I97V I103T F107L | W | W | W | R | W | W | W |
| G70S | W | W | R | R | W | R | R |
| F107L | W | W | R | R | W | R | R |
| E57G | W | W | R | R | R | R | R |
| A89V | W | W | R | R | W | R | R |
| I77L I3P V108A | W | W | W | W | W | W | W |
| I77L L135R | W | W | W | W | W | W | W |
| I77L S12R I103V | W | W | W | W | W | W | W |
| I77L E132A | W | W | W | W | W | W | W |
| I77L I3L L135R | W | W | W | W | W | W | W |
| I77L I3S E132A | W | W | W | W | W | W | W |
| I77L N127H E132A | W | W | W | W | W | W | W |

The Table shows mutants isolated from libraries of mutagenized CasTn3. The left-hand column gives the mutants, and the other columns show the phenotype of each mutant in the experiments described above. The results show that C1res1C2xsite I recombination requires the expression of NM resolvase, CasTn3 and two gRNA.

What is claimed is:

1. A polypeptide comprising:
   (i) a catalytically dead CRISPR-Cas domain having an amino acid sequence of SEQ ID NO. 1 with a D10A mutation and a second mutation selected from H840A, N854A, N863A; and
   (ii) a recombinase domain comprising a serine recombinase, wherein the serine recombinase is Tn3 (SEQ ID NO: 3) and wherein the recombinase domain has an amino acid sequence selected from the group consisting of SEQ ID NO: 5 and the following variants thereof:
   (a) I77L
   (b) F83L F107L
   (c) I3T D95E
   (d) G70S F107L
   (e) E57G A89V
   (f) K37R D44N
   (g) I97V I103T F107L
   (h) G70S
   (i) F107L
   (j) E57G
   (k) A89V
   (l) I77L I3P V108A
   (m) I77L L135R
   (n) I77L S12R I103V
   (o) I77L E132A
   (p) I77L I3L L135R
   (q) I77L I3S E132A; and
   (r) I77L N127H E132A.

2. The polypeptide of claim 1, further comprising a linker that links the CRISPR-Cas domain and the recombinase domain.

3. The polypeptide of claim 2, wherein the linker has an amino acid sequence of The-Ser.

4. A composition comprising: a first nucleotide sequence encoding the polypeptide of claim 1.

5. The composition of claim 4, further comprising a donor DNA comprising a transgene.

6. A method of integrating a transgene into the genome of a cell comprising introducing into the cell the composition of claim 4.

7. The method of claim 6, wherein the cell is a eukaryotic cell.

8. The method of claim 6, wherein the cell is a mammalian or human cell.

9. The method of claim 6, wherein the cell is a one-cell embryo.

* * * * *